(12) United States Patent
Bors et al.

(10) Patent No.: US 7,087,147 B2
(45) Date of Patent: *Aug. 8, 2006

(54) ELECTROACTIVE CATALYSIS

(75) Inventors: Daniel Arthur Bors, Maple Glen, PA (US); Anne Mae Gaffney, West Chester, PA (US); Stephen Gerard Maroldo, Ambler, PA (US)

(73) Assignee: Rohm and Haas Company, Philadelphia, PA (US)

( * ) Notice: Subject to any disclaimer, the term of this patent is extended or adjusted under 35 U.S.C. 154(b) by 253 days.

This patent is subject to a terminal disclaimer.

(21) Appl. No.: 10/720,521

(22) Filed: Nov. 25, 2003

(65) Prior Publication Data

US 2004/0104109 A1    Jun. 3, 2004

Related U.S. Application Data

(63) Continuation-in-part of application No. 10/294,205, filed on Nov. 14, 2002, now Pat. No. 7,001,500.

(60) Provisional application No. 60/331,920, filed on Nov. 20, 2001.

(51) Int. Cl.
*C25B 3/02* (2006.01)

(52) U.S. Cl. ............... 205/413; 205/462; 204/168; 204/169

(58) Field of Classification Search ........ 205/413–462; 204/168, 169
See application file for complete search history.

(56) References Cited

U.S. PATENT DOCUMENTS

| 5,281,745 | A | 1/1994 | Ushikubo et al. |
| 5,306,411 | A | 4/1994 | Mazanec et al. |
| 5,380,933 | A | 1/1995 | Ushikubo et al. |
| 5,472,925 | A | 12/1995 | Ushikubo et al. |
| 5,994,580 | A | 11/1999 | Takahashi et al. |
| 6,043,186 | A | 3/2000 | Komada et al. |
| 6,214,195 | B1 | 4/2001 | Yadav et al. |
| 6,267,864 | B1 * | 7/2001 | Yadav et al. ......... 205/341 |
| 2002/0014417 | A1 * | 2/2002 | Kuehnle et al. ...... 205/437 |

FOREIGN PATENT DOCUMENTS

| EP | 0512846 A | 11/1992 |
| EP | 0529853 A | 3/1993 |
| EP | 0767164 A | 4/1997 |

OTHER PUBLICATIONS

Abstract of Japanese Laid-Open Patent Application No. 6-228073.

* cited by examiner

*Primary Examiner*—Arun S. Phasge
(74) *Attorney, Agent, or Firm*—Marcella Bodner; Kenneth Crimaldi

(57) ABSTRACT

The application of an electric current to catalysts useful for the vapor phase oxidation of hydrocarbons allows for processes for obtaining enhanced catalytic processing of a given feed material with a given catalyst, processes allowing the ready change-over from one product of a given feed stream to another product of that feed stream without the need to change catalyst, and processes allowing the ready change over from one feed stream to another feed stream with the concomitant change over from one product to another product without the need to change catalyst.

9 Claims, 2 Drawing Sheets

ELECTROACTIVE CATALYSIS

CROSS REFERENCE TO RELATED PATENT APPLICATIONS

This non-provisional application is a continuation-in-part of non-provisional U.S. patent application Ser. No. 10/294,205, filed Nov. 14, 2002, now U.S. Pat. No. 7,001,500, benefit of which is claimed under 35 U.S.C. §120 and which in turn claims benefit under 35 U.S.C. §119(e) of U.S. provisional Application No. 60/331,920 filed Nov. 20, 2001, priority benefit of which is also claimed for the present continuation-in-part application.

The present invention relates, in general, to the vapor phase catalytic oxidation of hydrocarbons. More particularly, it relates to processes for obtaining enhanced catalytic processing of a given feed material with a given catalyst, to processes allowing the ready change-over from one product of a given feed stream to another product of that feed stream without the need to change catalyst, and to processes allowing the ready change over from one feed stream to another feed stream with the concomitant change over from one product to another product without the need to change catalyst.

The activation of certain catalysts by the passage of an electric current therethrough is known for the oxidation of methanol to carbon dioxide and water, or to carbon dioxide, water and hydrogen; for the oxidation of ethanol; for the oxidation of toluene and for the oxidation of ammonia. See U.S. Pat. No. 6,214,195 B1. However, it would be desirable to activate catalysts in industrially important processes such as the vapor phase catalytic partial oxidation of hydrocarbons (see U.S. Pat. Nos. 5,380,933 and 5,994,580) and the vapor phase catalytic ammoxidation of hydrocarbons (see U.S. Pat. No. 5,281,745 and Japanese Laid-Open Patent Application Publication No. 6-228073).

It is an object of the present invention to provide catalytic processes having enhanced catalytic processing of a given feed material with a given catalyst. It is a further object of the present invention to provide a process allowing the ready change-over from one product of a given feed stream to another product of that feed stream without the need to change catalyst. It is yet a further object of the present invention to provide a process allowing the ready change-over from one feed stream to another feed stream with the concomitant change-over from one product to another product without the need to change catalyst.

Thus, in a first aspect, the present invention provides a method for enhancing the production of an oxidative reaction product of a hydrocarbon comprising:

providing an electrically conductive catalyst composition comprising a vapor phase partial oxidation catalyst;

subjecting said electrically conductive catalyst composition to an electric current passing through said electrically conductive catalyst composition;

passing a hydrocarbon vapor over said electrically conductive catalyst composition;

wherein said vapor phase partial oxidation catalyst comprises a mixed metal oxide having the following empirical formula

wherein

A is at least one element selected from the group consisting of Mo and W,

M is at least one element selected from the group consisting of V and Ce,

N is at least one element selected from the group consisting of Te, Se and Sb,

X is at least one element selected from the group consisting of Nb, Ta, Ti, Al, Zr, Cr, Mn, Fe, Ru, Co, Rh, Ni, Pt, Bi, B, In, As, Ge, Sn, Li, Na, K, Cs, Fr, Be, Mg, Ca, Sr, Ba, Hf, Pb, P, Pm, Eu, Gd, Dy, Ho, Er, Th, Yb, Lu, Au, Ag, Pd, Ga, Pr, Re, Ir, Nd, Y, Sm and Tb, wherein when a=1, m=0.01 to 1.0, n=0.01 to 1.0, x=0.001 to 1.0 and o is dependent on the oxidation state of the other elements.

In a second aspect, the present invention provides a method for altering the oxidative reaction product of a vapor phase catalytic partial oxidation of a hydrocarbon comprising:

providing an electrically conductive catalyst composition comprising a vapor phase partial oxidation catalyst;

subjecting said electrically conductive catalyst composition to a first electric current passing through said electrically conductive catalyst composition, said first electric current favoring the production of a first oxidative reaction product of a hydrocarbon;

passing said hydrocarbon over said electrically conductive catalyst composition;

subjecting said electrically conductive catalyst composition to a second electric current passing through said electrically conductive catalyst composition, said second electric current favoring the production of a second oxidative reaction product of said hydrocarbon.

In a third aspect, the present invention provides a method for altering the oxidative reaction product of a vapor phase catalytic partial oxidation comprising:

providing an electrically conductive catalyst composition comprising a vapor phase partial oxidation catalyst;

subjecting said electrically conductive catalyst composition to a first electric current passing through said electrically conductive catalyst composition, said first electric current favoring the production of an oxidative reaction product of a first hydrocarbon by a vapor phase catalytic oxidation reaction;

passing said first hydrocarbon over said electrically conductive catalyst composition;

ceasing passage of said first hydrocarbon over said electrically conductive catalyst composition;

subjecting said electrically conductive catalyst composition to a second electric current passing through said electrically conductive catalyst composition, said second electric current favoring the production of an oxidative reaction product of a second hydrocarbon;

passing said second hydrocarbon over said electrically conductive catalyst composition.

In a fourth aspect, the present invention provides a method for enhancing the production of an oxidative reaction product of a hydrocarbon comprising:

providing an electrically conductive catalyst composition comprising a vapor phase partial oxidation catalyst;

subjecting said electrically conductive catalyst composition to an electric current passing through said electrically conductive catalyst composition;

passing an oxidative gas over said electrically conductive catalyst;

then, passing a hydrocarbon vapor over said electrically conductive catalyst composition.

These and other aspects of the present invention will be more clearly understood by reference to the accompanying drawing figures wherein.

Figure 1:
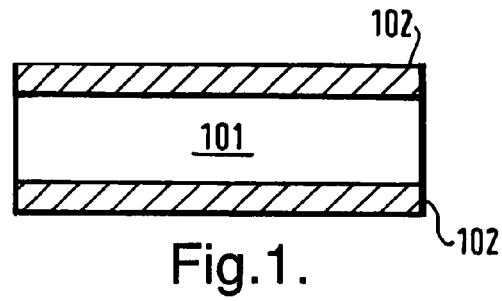
FIG. 1 illustrates a layer of catalyst sandwiched between two electrodes.

In general, the present invention involves the chemical transformation of a substance by the use of a catalyst and an electric current. The catalyst or a composition containing the catalyst interacts with an applied electric field to produce a current. Preferably, a high surface area form of the catalyst or the composition containing the catalyst is utilized, i.e. forms having a surface area of greater than 1 $cm^2/g$, more preferably greater than 100 $cm^2/g$, and most preferably greater than 1 $m^2/g$. The catalyst or the composition containing the catalyst is preferably formed into a single layer or multilayer structure. The substance to be chemically transformed is exposed to the catalyst or the composition containing the catalyst, the catalyst or the composition containing the catalyst having or having had an electric field or potential induced in the catalyst or the composition containing the catalyst by an applied electric current.

The catalyst or a composition containing the catalyst preferably has a high band gap, i.e. a band gap greater than 0.5 eV, more preferably a band gap greater than 1.5 eV, most preferably a band gap greater than 2.5 eV. As previously noted, the catalyst or the composition containing the catalyst is preferably provided in a high surface area form. Preferably, this form is as a nanostructured material or a nanocomposite or a high internal porosity material. Moreover, a porous structure comprising at least one layer of the catalyst or the composition containing the catalyst and electrodes positioned on the at least one layer to enable an electric field to be applied across the at least one layer is preferred. It is further preferred that the resistance between the electrodes be between 0.001 milliohm and 100 megaohm per unit ampere of current flowing through the structure, more preferably between 0.01 milliohm to 10 megaohm per unit ampere flowing through the structure, most preferably between 1 milliohm and 1 megaohm per unit ampere of current flowing through the structure. Nonetheless, higher resistances may be utilized when the chemical transformation step so requires.

In those cases where the current flow measure is not known or difficult to measure, it is preferred that the corresponding power consumption levels for the device be used to practice this invention. For example, in the case of the external application of an electric field, then it is preferred that the power consumption due to device operation be between 0.001 milliwatt and 100 megawatt. While miniature, thin film and micromachined devices may utilize less power than these levels and some applications may utilize more power than these levels, and these higher and lower power consumptions are included within the scope of the present invention, in all cases, designs and/or operations that lead to lower power consumption are favored so as to minimize the operating costs. In the case where alternating current is utilized, the overall impedance of the device should be kept low to reduce energy consumption and operating costs. Similarly, in the case where direct current is utilized, the overall resistance of the device should be kept low to reduce energy consumption and operating costs.

Operation of the invention is effected by placing the catalyst or the composition containing the catalyst in a direct current or alternating current electrical circuit that leads to flow of charge. The charge flow can be through flow of electrons, flow of ions or flow of holes. Various modes of operation are possible, including, but not limited to, charge flow being initiated prior to the flow of reactant(s) and reactant(s) flow being initiated prior to charge flow. During operation, heat transfer (heating or cooling) and pressure control (superatmospheric, atmospheric and subatmospheric) may be effected by conventional means. Moreover, operations may be in steady or unsteady state, utilizing a constant electric field or application of an electric field in the form of symmetric or unsymmetric wave forms.

In an embodiment of the invention in which the catalyst or the composition containing the catalyst is exposed to an electric field prior to contact with at least one hydrocarbon reactant, contact with the electric field may occur at several points during the synthesis and preparation of the catalyst or the composition containing the catalyst. For example, an electric field may be made to interact with the calcined catalyst, the dried catalyst prior to calcination, and the precursor solutions and gels. In addition, the electric field may be applied during the processes of mixing precursor solutions, drying the precursor and calcination. Methods for causing an electric field to interact with the catalyst or the composition containing the catalyst include, for example, causing the catalyst or the composition containing the catalyst to flow through a channel in which it is subjected to an electric field (e.g., an electrostatic spray process), and causing an electric current to flow through the catalyst or the composition containing the catalyst (in bulk, or on a support). In addition, electrodes may be placed within the precursor solution vessels and precursor mixing vessels, the catalyst drying bed and the catalyst oxidation bed to cause an electric field or current to interact with the catalyst.

The following definitions will be used in describing the present invention:

"Catalysis" is the acceleration of any physical or chemical reaction by a small quantity of a substance—referred to hereinafter as "catalyst"—the amount and nature of which remain essentially unchanged during the reaction. Alternatively, the term includes applications where the catalyst can be regenerated or its nature essentially restored after the reaction by any suitable means such as, but not limited to, heating, pressure, oxidation or reduction. A reactant is considered to be catalyzed by a substance if the substance is a catalyst for one or more intermediate steps in the associated physical or chemical change of the reactant into a product.

"Chemical transformation" is the rearrangement, change, addition or removal of chemical bonds in any substance or substances.

"Nanomaterials" are substances having a domain size of less than 250 nm, preferably less than 100 nm, or, alternatively, having a domain size sufficiently small that a selected material property is substantially different, e.g., different in kind or magnitude, from that of a micron-scale material of the same composition due to size confinement effects. For example, a property may differ by about 20% or more from the same property for an analogous micron-scale material. In the case that the domain size may be difficult to measure or difficult to define, such as in porous networks, this term refers to materials that have a surface area of greater than 1 $cm^2/g$. The term includes coated, partially coated, fully coated, island, uncoated, hollow, porous and dense domains. These materials may be produced by any method for use in the present invention.

"Domain size" is the minimum dimension of a particular material morphology. For example, the domain size of a powder is the particle size, the domain size of a whisker or fiber is the diameter and the domain size of a film or plate is the thickness.

"Confinement size" of a material, as the term is used herein in reference to a fundamental or derived property of interest, is the mean domain size below which the property becomes a function of the domain size of the material.

"Activity" of a catalyst is a measure of the rate of conversion of the starting material by the catalyst.

"Selectivity" of a catalyst is a measure of the relative rate of formation of each product from two or more competing reactions.

"Stability" of a catalyst is a measure of the catalyst's ability to retain useful life, activity and selectivity above predetermined levels in the presence of factors (such as, but not limited to, coking, poisoning, oxidation, reduction, thermal run-away, expansion-contraction, flow, handling and charging of catalyst) that can cause chemical, thermal, or mechanical degradation or decomposition.

"Porous" means a structure with sufficient interstitial space to allow transport of reactant(s) and product(s) within the structure to expose the reactant(s) to the constituent compositions making up the porous structure.

"Favoring" means, in the context of the application of an electric current to an electrically conductive catalyst composition, the alteration of the catalyst so as to produce a given product that would not be produced by that catalyst if it had not been so treated or so as to produce a given product in an enhanced yield, selectivity and/or rate of production as compared with that which would be produced by that catalyst if it had not been so treated.

FIG. 1 illustrates an embodiment of the present invention in its most basic form. Essentially, a catalyst layer 101 is sandwiched between two electrodes 102. Catalyst layer 101 comprises a material that either as applied or as later modified by post processing acts as a catalyst for the conversion of a particular feed composition into a desired product composition. The dimensions and geometry of the catalyst layer 101 are selected to provide both sufficient exposure to a feed composition and to allow an impeded current flow between electrodes 102 when an electric field is applied across electrodes 102. The properties of the catalyst layer 101 are selected to allow the catalyst layer 101 to both support an electric field and conduct current. It is not necessary that the catalyst layer 101 be active as a catalyst at ambient conditions. However, the catalyst layer 101 may have catalytic activity in ambient or non-ambient conditions even when an electric field is not applied between the electrodes 102.

Figure 2:
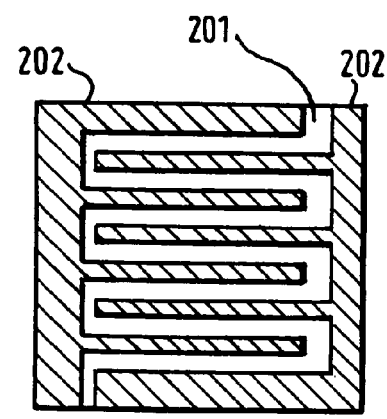
FIG. 2 illustrates an alternate embodiment wherein the catalyst layer and the two electrodes form a multilayer or interdigitated structure.

FIG. 2 illustrates a preferred alternative configuration in which electrodes 202 and active layer 201 are arranged in a multilayer or interdigitated structure. The structure shown in FIG. 2 provides greater surface area between electrodes 202 and catalyst layer 201 as compared to the embodiment illustrated in FIG. 1.

In case the resistive component between the electrodes 202 is the mechanistic impedance limiting the performance of the device, the parallel multilayer structure shown in FIG. 2 can reduce the impedance of the chemical transformation device in accordance with the present invention. The individual active layers 101 or electrodes can be the same or different formulation. It is contemplated that one or more active layers 101 may be replaced by a material capable of a secondary but desired function. For example, one active layer 101 can be replaced with a resistive composition by design to provide heat to the device. In some embodiments, it may be desirable to have one or more active layers replaced with electromagnetic interference filter layers to shield the active layer from inductively or capacitively coupling with the environment. In another embodiment, one of the layers can be air or an insulating layer in order to provide thermal isolation of the active layer. In yet another embodiment, sensing layers may be provided to sense the concentration of one or more species in the feed or processed stream. In yet another embodiment, electrochemical couple layers may be provided to internally generate electricity and energy needed to satisfactorily operate the device. In other embodiments, the electrode layers can function as anodes and cathodes.

The method for preparing a chemical composition transformation device in accordance with the present invention involves selecting an active material comprising a surface that physically or chemically interacts with the substance that is desired to be transformed or with one of the intermediates of such substance. The active material is preferably prepared in a high surface area form, i.e. a form that has a surface area of greater than 1 $cm^2/g$, preferably greater than 100 $cm^2/g$, more preferably greater than 1 $m^2/g$.

The active material is usually prepared as a powder or a powder mixture. This powder or powder mixture can then be formed into a structure. Alternatively, the powder or powder mixture may be blended with additional materials to form a slurry, an ink or a paste; and such a composition can then be used to form an appropriate structure. The structure may be formed by any method or combination of methods, including, but not limited to, spin coating, dip coating, surface coating a porous structure, powder pressing, casting, screen printing, tape forming, precipitation, sol-gel forming, curtain deposition, physical sputtering, reactive sputtering, physical vapor deposition, chemical vapor deposition, ion beam, e-beam deposition, molecular beam epitaxy, laser deposition, plasma deposition, electrophoretic deposition, magnetophoretic deposition, thermophoretic deposition, stamping, cold pressing, hot pressing, pressing with an additive and then removal of the additive by heat or solvents or supercritical fluids, centrifugal casting, gel casting, investment casting, extrusion, electrochemical or electrolytic or electroless deposition, screen printing, stacking and laminating, brush painting or self-assembly. In any event, the active material containing structure can be formed as free standing structure or on a substrate.

The active layer structure may be porous or non-porous. However, it is preferred that the active layer structure be porous to reduce pressure drop and enhance contact of the active material with the chemical species of interest. In other embodiments, the structure may be smooth or wavy, flexible or rigid, homogeneous or heterogeneous, doped or undoped, flat or cylindrical, or any other shape and form, nanostructured or non-nanostructured. The active layer structure may be in film form, dispersed particle form, bulk form or wire form. The cross-sectional area of the active material structure can be from a few square microns to thousands of square meters depending on the particular application. The active material can also be doped with available promoters and additives to further enhance the device's performance. The active material can also be mixed with inert elements and compositions and insulating formulations to further reduce capital and/or operating costs.

The electrode structure, illustrated in FIG. 1 and FIG. 2 as 102 and 202, respectively, may comprise any composition with a lower impedance, in the case of an AC current, or a lower resistance, in the case of a DC current, than the active material composition. The composition of the electrode layer may include, but is not limited to, organic materials, inorganic materials, metallic, alloy, ceramic, polymer, non-metallic, ceramic-ceramic composite, ceramic-polymer composite, ceramic-metal composite, metal-polymer composite, polymer-polymer composite, metal-metal composite, or a combination of one or more of these. Geometries may be porous or dense, flat or tapered, uniform or non-uniform, planar or wavy, straight or curved, patterned or non-patterned, micron or sub-micron, grain size confined or not, or a combination of two or more of these.

Figure 3:
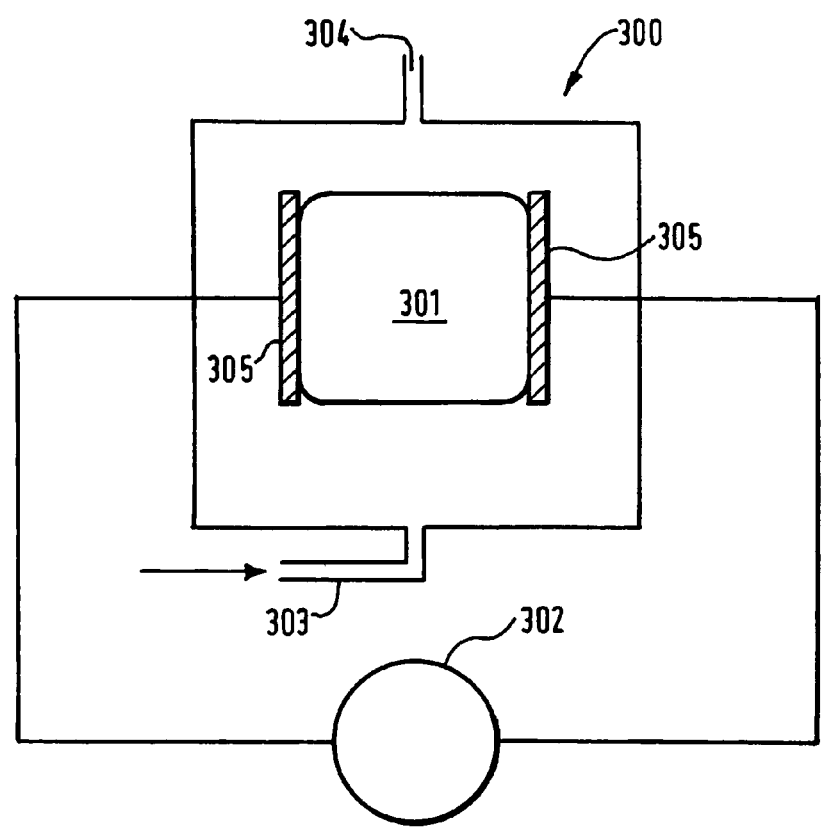
FIG. 3 is a schematic representation of a chemical reactor for use with the processes of the present invention.

FIG. 3 illustrates an exemplary reactor 300 for use with the processes of the present invention. The electrodes 305 are coupled in a circuit with power supply 302 so as to apply an electric field between the opposing electrodes 305 of the reactor. The circuit shown in FIG. 3 is merely illustrative; it may be replaced with any suitable circuit that can provide a flow of charge, internally (such as, but not limited to, ohmic or ion flow or hole flow based current) or externally (such as, but not limited to, eddy current or induced current from an applied field) or both, in a given application. Power supply 302 may supply direct current, alternating current, or any other waveform. The current may be induced to flow in the device when the device is wired or through the use of wireless techniques. In a typical operation, the applied power is less than 15 watts per gram of catalyzing substance.

The device 301 may include a single element such as shown in FIG. 1 or FIG. 2 or an array of such elements. The electrodes of the device(s) 301 may alternatively provide means to connect the device to induce interaction with an externally induced field such as but not limited to radio frequency or microwave frequency waves, or the equivalent.

Reactor 300 includes an inlet port 303 for receiving a feed stream and an outlet 304 for a product stream. In one exemplary operation, feed gas passes in contact with the device 301 while power supply 302 is active and is transformed before passing from outlet 304. In another exemplary operation, feed gas passes in contact with the device 301 after the power supply 302 has been shut down and is transformed before passing from outlet 304. Device 301, shown in FIG. 3, may be placed in reactor 300 in various ways, such as, but not limited to, as a randomly or periodically arranged packed bed, with or without baffles to prevent short circuiting of feed, inside pipes, heated or cooled, pressurized or evacuated, isothermal or non-isothermal, adiabatic or non-adiabatic, or straight flow or recycle reactor.

FIGS. 4A, 4B, 4C and 4D illustrate a preferred form of a reactor, i.e. a microchannel reactor, for use in the present invention. As may be seen in FIG. 4A, the reactor 400 comprises an inlet 401 for gaseous reactant(s), an outlet 402 for gaseous product(s) and any unconverted reactant(s), a reactor body section 403 containing a catalyst structure 404, a transition zone 405 connecting inlet 401 and reactor body section 403, and a transition zone 406 connecting reactor body section 403 and outlet 402. The catalyst structure 404 is disposed in reactor body section 403 so that any gaseous reactant(s) entering through inlet 401 must pass through catalyst structure 404 before exiting the reactor through outlet 402.

Figure 4A:
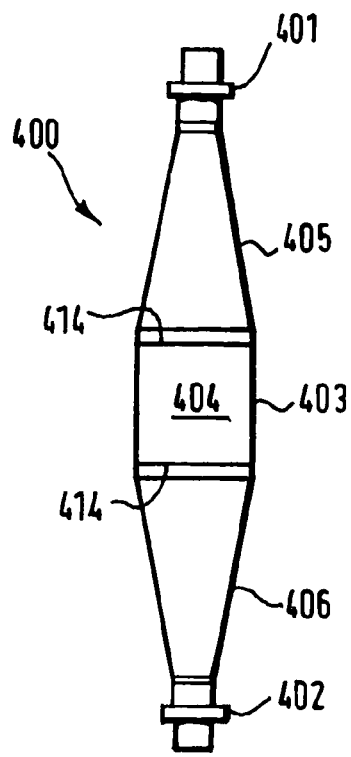
FIGS. 4A, 4B, 4C and 4D illustrate a microchannel reactor utilizable with the processes of the present invention.
Figure 4B:
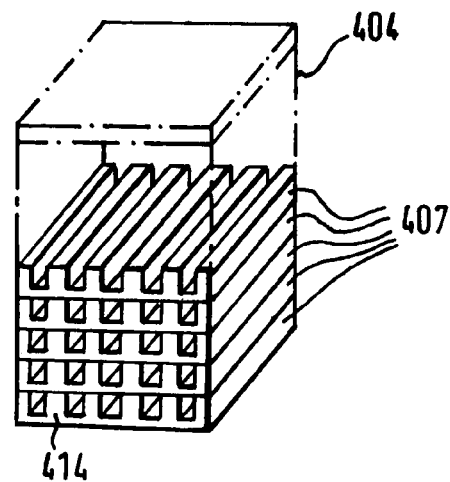
Figure 4C:
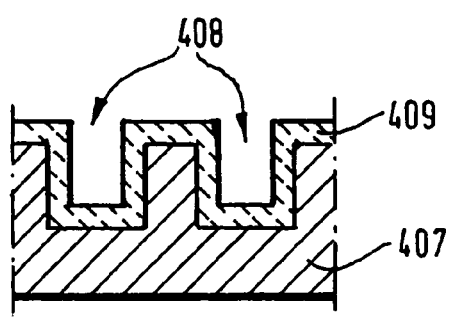
Figure 4D:
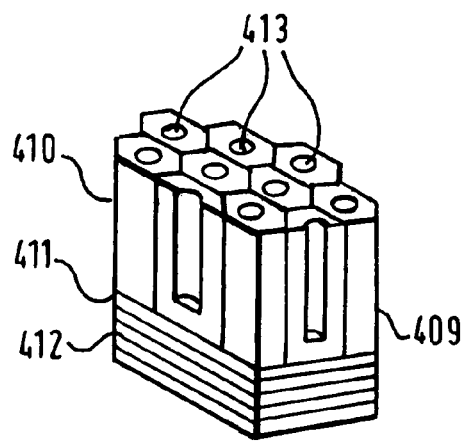

The catalyst structure 404 is preferably formed by a plurality of stacked wafers 407, as may best be seen in FIG. 4B. Each wafer 407 has a plurality of channels 408 formed therein, as best seen in FIG. 4C, that run the length of the wafer. The channels have lengths on the order of millimeters, i.e. from 10 to 100 millimeters, e.g., 30 millimeters, and cross-sectional dimensions on the order of microns, i.e. from 10's of microns to 100's of microns, e.g., 200 microns×200 microns. The channels 408 may have a porous surface layer 409 therein. As best seen in FIG. 4D, this porous surface layer 409, e.g., for the case of aluminum/aluminum oxide, may comprise a layer of porous aluminum oxide 410, a layer of non-porous aluminum oxide 411 and a layer of aluminum 412. The pores 413 may have pore diameters of 10–30 nm, pore lengths of 0.5–40 nm and a pore density of up to $10^{14}$–$10^{15}$ pores/m$^2$.

Electrodes 414 may be formed as a coating on each of the opposed ends of wafers 407.

In operation, a solution of the desired catalytic material may be wash-coated on the porous surfaces 409 of the channels 408 and then dried. One or more wash coats may be utilized as needed.

Alternatively, if the channels 408 have a non-porous surface a nano-structured catalytic composition may be coated on the channel surfaces. The use of a non-porous surface eliminates pore diffusion limitations. Any suitable means for coating catalytic nano-particles on a surface may be utilized.

As a further alternative, a monolithic support may be utilized in lieu of the previously described stacked wafers of the microchannel reactor. Such a monolithic support has numerous substantially parallel channels that pass through the monolith. The monolith may be in the form of a honeycomb structure wherein the channel sizes typically range from about 1.5 to 100 cells/cm$^2$ of monolith frontal area, e.g., from about 8 to 50 cells/cm$^2$ of monolith frontal area wherein each cell has a width opening ranging from 0.29 to 0.13 cm, respectively. A typical 30 cells/cm$^2$ honeycomb structure has about 4600 m$^2$ of geometric wall area per cubic meter of monolith volume. The shape of the cross-section of a honeycomb cell is not limited and may include circles, squares, triangles, other regular geometric shapes, as well as irregular shapes. Typically, the monolith is formed of a ceramic material although other materials are possible, e.g., metals such as stainless steel. The catalytic materials may be coated on the interior walls of the channels in the monolith or deposited in the channels as a nanomaterial by the techniques noted above.

With respect to such catalysts, the present invention has been found to be useful in the oxidative conversion of hydrocarbons into products, particularly partially oxidized products. Some illustrative reactions and catalysts are listed in the following tabulation.

| Reaction | Catalyst |
| --- | --- |
| ethylene → ethylene oxide | Ag/support |
| propene or isobutene → unsaturated aldehyde | Cu$_2$O, Bi molybdate |
| o-xylene, naphthalene → phthalic anhydride | V$_2$O$_5$, V$_2$O$_5$/TiO$_2$, V$_2$O$_5$—K$_2$S$_2$O$_7$/SiO$_2$ |
| butane or butene → maleic anhydride | V$_2$O$_5$—P$_2$O$_5$/support |
| benzene → maleic anhydride | V$_2$O$_5$, V$_2$O$_5$—MoO$_3$, P$_2$O$_5$/support |
| propene + NH$_3$ → acrylonitrile | Bi molybdate, U-Sb oxides |
| isobutene + NH$_3$ → methacrylonitrile | multicomponent oxide |
| toluene + NH$_3$ → benzonitrile | V$_2$O$_5$—MoO$_3$/Al$_2$O$_3$ |
| m-xylene + NH$_3$ → isophthalonitrile | V$_2$O$_5$—MoO$_3$/Al$_2$O$_3$ |
| o-xylene + NH$_3$ → phthalonitrile | V$_2$O$_5$—Sb$_2$O$_5$ |
| 3- or 4-picoline + NH$_3$ → 3- or 4-cyanopyridine | V$_2$O$_5$—MoO$_3$/Al$_2$O$_3$ |
| methane + NH$_3$ → HCN | Pt-Rh wire gauze |
| ethylene + HCl → vinyl chloride | CuCl$_2$/Al$_2$O$_3$ |
| propane → propene | mixed metal oxide |
| propane → acrolein | mixed metal oxide |
| propane → acrylic acid (AA) | mixed metal oxide |

| Reaction | Catalyst |
|---|---|
| isobutane → isobutene | mixed metal oxide |
| isobutane → methacrolein | mixed metal oxide |
| isobutane → methacrylic acid (MAA) | mixed metal oxide |
| propane + $NH_3$ → acrylonitrile | mixed metal oxide |
| isobutane + $NH_3$ → methacrylonitrile | mixed metal oxide |

The mixed metal oxides useful in the present invention have the empirical formula $$A_a M_m N_n X_x O_o$$

wherein A is at least one element selected from the group consisting of Mo and W, M is at least one element selected from the group consisting of V and Ce, N is at least one element selected from the group consisting of Te, Se and Sb, X is at least one element selected from the group consisting of Nb, Ta, Ti, Al, Zr, Cr, Mn, Fe, Ru, Co, Rh, Ni, Pt, Bi, B, In, As, Ge, Sn, Li, Na, K, Rb, Cs, Fr, Be, Mg, Ca, Sr, Ba, Hf, Pb, P, Pm, Eu, Gd, Dy, Ho, Er, Th, Yb, Lu, Au, Ag, Pd, Ga, Pr, Re, Ir, Nd, Y, Sm and Tb; and wherein, when $a=1$, $m=0.01$ to 1.0, $n=0.01$ to 1.0, $x=0.001$ to 1.0 and o is dependent on the oxidation state of the other elements.

Preferably, when $a=1$, $m=0.1$ to 0.5, $n=0.05$ to 0.5 and $x=0.001$ to 0.5. In one embodiment of the invention, when $a=1$, $m=0.15$ to 0.45, $n=0.05$ to 0.45, $x=0.01$ to 0.1. In another embodiment of the invention, when $a=1$, $m=0.2$ to 0.45, $n=0.2$ to 0.45, $x=0.001$ to 0.2. The value of o, i.e. the amount of oxygen present, is dependent on the oxidation state of the other elements in the catalyst. However, o is typically in the range of from 3 to 4.7.

In a preferred embodiment of the invention X is at least one element selected from among Nb, Ta, Ti, Al, Zr, Ni, Bi, Au, Ag, Pd, Ga, Re, Ir and Sm. In this embodiment, preferably, M is V and N is Te; more preferably X represents Nb and at least one second element Y, wherein Y is selected from among Ni, Bi, Au, Ag and Pd, giving the formulas $Mo_a V_m Te_n Nb_x Y_x O_o$ and $W_a V_m Te_n Nb_x Y_x O_o$ wherein a, m, n, x and o are as previously defined, and x may have a different value within the defined range as a subscript for Nb than it has as a subscript for Y, and if more than one Y is present, x may be different for each Y. Particularly preferred promoted mixed metal oxides have the empirical formulae $Mo_a V_m Te_n Nb_x Pd_x O_o$ and $W_a V_m Te_n Nb_x Pd_x O_o$.

The mixed metal oxides can be prepared in the following manner.

In a first step a slurry or solution may be formed by admixing metal compounds, preferably at least one of which contains oxygen, and at least one solvent in appropriate amounts to form the slurry or solution. Preferably, a solution is formed at this stage of the catalyst preparation. Generally, the metal compounds contain elements A, M, N, X, and O, as previously defined.

Suitable solvents include water; alcohols including, but not limited to, methanol, ethanol, propanol, and diols, etc.; as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed, and not a slurry, at the time of mixing.

For example, when a mixed metal oxide of the formula $Mo_a V_m Te_n Nb_x O_o$ wherein the element A is Mo, the element M is V, the element N is Te and the element X is Nb, is to be prepared, an aqueous solution of niobium oxalate may be added to an aqueous solution or slurry of ammonium heptamolybdate, ammonium metavanadate and telluric acid, so that the atomic ratio of the respective metal elements would be in the prescribed proportions.

Once the aqueous slurry or solution (preferably a solution) is formed, the water is removed by any suitable method, known in the art, to form a catalyst precursor. Such methods include, without limitation, vacuum drying, freeze drying, spray drying, rotary evaporation and air drying. Vacuum drying is generally performed at pressures ranging from 10 mmHg to 500 mmHg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or air drying are generally preferred.

Alternatively, the catalyst component solution can be wash coated onto the porous wafers of a microchannel reactor, as illustrated in FIGS. 4A, 4B, 4C and 4D, and dried by any suitable means, so as to produce catalyst precursor coated wafers.

As a further alternative, the metal components of the presently contemplated catalyst may be supported on materials such as alumina, silica, silica-alumina, zirconia, titania, etc. by conventional incipient wetness techniques. In one typical method, solutions containing the metals are contacted with the dry support such that the support is wetted; then, the resultant wetted material is dried, for example, at a temperature from room temperature to 200° C. In another method, metal solutions are contacted with the support, typically in volume ratios of greater than 3:1 (metal solution: support), and the solution agitated such that the metal ions are ion-exchanged onto the support.

Once obtained, the catalyst precursor is calcined. The calcination may be conducted in an oxygen-containing atmosphere or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired mixed metal oxide.

In a preferred mode of operation, the catalyst precursor is calcined in two stages. In the first stage, the catalyst precursor is calcined in an oxidizing environment (e.g. air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for 15 minutes to 8 hours, preferably for from 1 to 3 hours. Optionally, a reducing gas, such as, for example, ammonia or hydrogen, may be added during the second stage calcination.

In a particularly preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, in the case of a particulate catalyst, it is advantageous to conduct the calcination in a bed with continuous flow of the desired gas(es) through the bed of solid catalyst precursor particles.

With calcination, a catalyst is formed having the formula $A_aM_mN_nX_xO_o$ wherein A, M, N, X, 0, a, m, n, x and o are as previously defined.

The starting materials for the above promoted mixed metal oxide are not limited to those described above. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

The mixed metal oxide thus obtained may be used by itself as a solid catalyst, but may be formed into a catalyst together with a suitable carrier such as silica, alumina, titania, aluminosilicate, diatomaceous earth or zirconia.

The present invention is further directed to a process for preparing an electroactive catalyst, in which the above-described process for preparing a mixed metal oxide is performed with electroactivation of the mixed metal oxide being performed by exposure to an electric field during or after preparation of the mixed metal oxide, as described above.

In one embodiment, the present invention provides a process for producing an unsaturated carboxylic acid, which comprises subjecting an alkane, or a mixture of an alkane and an alkene, to a vapor phase catalytic oxidation reaction in the presence of a catalyst containing the above mixed metal oxide, while passing an electric current therethrough, to produce an unsaturated carboxylic acid.

In another embodiment, the present invention provides a process for producing an unsaturated carboxylic acid, which comprises subjecting an alkane, or a mixture of an alkane and an alkene, to a vapor phase catalytic oxidation reaction in the presence of a catalyst containing the above mixed metal oxide, wherein an electric current has been passed therethrough prior to commencement of said vapor phase catalytic oxidation reaction to produce an unsaturated carboxylic acid.

Of course, a combined embodiment is also possible wherein the electric current is passed through the electrically conductive catalyst composition prior to and during said vapor phase catalytic oxidation reaction.

In the production of such an unsaturated carboxylic acid, it is preferred to employ a starting material gas which contains steam. In such a case, as a starting material gas to be supplied to the reaction system, a gas mixture comprising a steam-containing alkane, or a steam-containing mixture of alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

Further, as a diluting gas, an inert gas such as nitrogen, argon or helium may be supplied. The molar ratio (alkane or mixture of alkane and alkene): (oxygen): (diluting gas): ($H_2O$) in the starting material gas is preferably (1): (0.1 to 10): (0 to 20): (0.2 to 70), more preferably (1): (1 to 5.0): (0 to 10): (5 to 40).

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a $C_{3-8}$ alkane, particularly propane or isobutane. According to the present invention, from such an alkane, an unsaturated carboxylic acid such as an α, β-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is preferred to employ a mixture of $C_{3-8}$ alkane and $C_{3-8}$ alkene, particularly propane and propene or isobutane and isobutene. According to the present invention, from such a mixture of an alkane and an alkene, an unsaturated carboxylic acid such as an α, β-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably at least 1.0% by weight to 95% by weight; most preferably, 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above promoted mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane, or a mixture of an alkane and an alkene, substantially in the absence of molecular oxygen for the vapor phase catalytic reaction. In such a case, a method may be adopted wherein periodically the catalyst is regenerated by contact with an oxidative gas, such as oxygen, air or nitrogen monoxide. An electric current may be passed through the catalyst prior to contact with the oxidative gas and/or during contact with the oxidative gas.

The present invention will be described in further detail with respect to a case where propane is used as the starting material alkane and air is used as the oxygen source. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 400° C. (It should be borne in mind that the use of a microchannel reactor, as previously described, provides enhanced heat control. For instance, in constructing the microchannel reactor, wafers containing channels with catalyst disposed therein may be alternated with wafers containing channels for passage of a heat transfer fluid therethrough. This puts the heat transfer fluid in very close proximity to the source of heat whereby the overall transfer of heat is speeded up due to thinner walls inhibiting such transfer.); the gas space velocity, SV, in the vapor phase reaction is usually within a range of from 100 to 10,000 hr$^{-1}$, preferably 300 to 6,000 hr$^{-1}$, more preferably 300 to 2,000 hr$^{-1}$; the average contact time with the catalyst can be from 0.01 to 10 seconds or more, but is usually in the range of from 0.1 to 10 seconds, preferably from 2 to 6 seconds (It should be borne in mind that the use of a microchannel reactor, as previously described, provides a ready capability for short contact times, i.e. contact times of no more than 100 milliseconds, preferably no more than 50 milliseconds, more preferably no more than 20 milliseconds, still more preferably no more than 10 milliseconds, yet still more preferably no more than 5 milliseconds. Such short contact times help to inhibit secondary reactions of the desired products of the catalytic oxidation.); the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. (It should be borne in mind that the use of a microchannel reactor, as previously described, allows operation within the explosive range.) Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem which enables the attainment of higher selectivity to the desired products. The catalyst of the present invention operates more efficiently at the lower temperature range set forth above, significantly reducing the formation of acetic acid and carbon oxides, and increasing selectivity to acrylic acid. (The use of a microchannel reactor, as previously described, improves selectivity of the reaction, also.) As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid.

In yet another embodiment, the method of the present invention comprises subjecting an alkane, or a mixture of an alkane and an alkene, to a vapor phase catalytic partial oxidation reaction with ammonia in the presence of a catalyst containing the above mixed metal oxide, while passing an electric current therethrough, to produce an unsaturated nitrile.

In still another embodiment, the present invention provides a process for producing an unsaturated nitrile, which comprises subjecting ammonia and an alkane, or a mixture of an alkane and an alkene, to a vapor phase catalytic oxidation reaction in the presence of a catalyst containing the above mixed metal oxide, wherein an electric current has been passed therethrough prior to commencement of said vapor phase catalytic oxidation reaction, to produce an unsaturated nitrile.

In the production of such an unsaturated nitrile, as the starting material alkane, it is preferred to employ a $C_{3-8}$alkane such as propane, butane, isobutane, pentane, hexane and heptane. However, in view of the industrial application of nitriles to be produced, it is preferred to employ a lower alkane having 3 or 4 carbon atoms, particularly propane and isobutane.

Similarly, as the starting material mixture of alkane and alkene, it is preferred to employ a mixture of $C_{3-8}$alkane and $C_{3-8}$alkene such as propane and propene, butane and butene, isobutane and isobutene, pentane and pentene, hexane and hexene, and heptane and heptene. However, in view of the industrial application of nitriles to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the ammoxidation reaction of this aspect of the present invention is not clearly understood. However, the oxidation reaction is conducted by the oxygen atoms present in the above promoted mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas, However, a gas mixture comprising an alkane or a mixture of an alkane and an alkene and ammonia, and an oxygen-containing gas may be supplied alternately.

It is also possible to use only ammonia and an alkane, or a mixture of an alkane and an alkene, substantially in the absence of molecular oxygen for the vapor phase catalytic reaction. In such a case, a method may be adopted wherein periodically the catalyst is regenerated by contact with an oxidative gas, such as oxygen, air or nitrogen monoxide. An electric current may be passed through the catalyst prior to contact with the oxidative gas and/or during contact with the oxidative gas.

The ammoxidation of the present invention will be described in further detail with respect to a case where propane is used as the starting material alkane and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The ammoxidation process of the present invention may be conducted at a temperature of, for example, from 250° C. to 480° C. More preferably, the temperature is from 300° C. to 400° C. The gas space velocity, SV, in the gas phase reaction is usually within the range of from 100 to 10,000 $hr^{-1}$, preferably from 300 to 6,000 $hr^{-1}$, more preferably from 300 to 2,000 $hr^{-1}$. As a diluent gas, for adjusting the space velocity and the oxygen partial pressure, an inert gas such as nitrogen, argon or helium can be employed. When ammoxidation of propane is conducted by the method of the present invention, in addition to acrylonitrile, carbon monoxide, carbon dioxide, acetonitrile, hydrocyanic acid and acrolein may form as by-products.

In its first aspect, the present invention provides a method for enhancing the output of a mixed metal oxide catalyst by passing an electric current therethrough to increase the activity and/or selectivity of the mixed metal oxide catalyst, thereby increasing the yield of a desired product, e.g., acrylic acid being produced by a vapor phase catalytic partial oxidation of propane. The electric current may be passed through the catalyst prior to and/or during use of the catalyst. The electric current may also be applied to the catalyst continuously or periodically prior to and/or during use of the catalyst.

In its second aspect, the present invention provides a method for altering the oxidative reaction product of a vapor phase catalytic partial oxidation of a hydrocarbon. For example, in the vapor phase catalytic partial oxidation of propane to acrylic acid, in addition to acrylic acid, other materials found in the product stream include propene and the unsaturated aldehyde acrolein. Thus, it is believed that the propane reacts in a series of steps, i.e. the propane is oxidatively dehydrogenated to propene, the propene is partially oxidized to acrolein and the acrolein is further oxidized to acrylic acid. By the present invention, the formation of the final reaction product or any of the intermediate reaction products may be controlled by selection of the current used to treat the catalyst. In this regard, when running the process with a catalyst that has been treated with a first current passing therethrough, a first desired reaction product can be obtained; however, at some later stage, the catalyst may be treated with a second current which favors the formation of a second reaction product different from the first reaction product. In this manner, a quick product changeover can be effected without the need to change catalyst. As with the first aspect of the present invention, electric current may be passed through the catalyst prior to and/or during use of the catalyst. The electric current may also be applied to the catalyst continuously or periodically prior to and/or during use of the catalyst. Similarly, in its third aspect, the present invention provides the ability to change the feed stream being fed to a catalyst so as to change the product being formed by the reaction. For example, it is not untypical for a manufacturer of acrylic acid to also be a manufacturer of methacrylic acid. It would be desirable from an equipment utilization point of view for the manufacturer to be able to use a single reactor train to produce both products. Thus, the present invention affords the opportunity to run a reactor train, containing a single catalyst bed, to produce acrylic acid from propane, when operating with a catalyst treated with a first current passing therethrough, and then to switch over to producing methacrylic acid from isobutane by changing the feed stream and operating with the catalyst which has been treated with a second current passing therethrough without the need to change catalyst. Once again, as with the first aspect of the present invention, electric current may be passed through the catalyst prior to and/or during use of the catalyst. The electric current may also be applied to the catalyst continuously or periodically prior to and/or during use of the catalyst.

Finally, in its fourth aspect, the present invention provides a method for enhancing the output of a mixed metal oxide catalyst by passing an electric current therethrough to increase the activity and/or selectivity of the mixed metal oxide catalyst, thereby increasing the yield of a desired product, e.g., acrylic acid being produced by a vapor phase catalytic partial oxidation of propane. The electric current may be passed through the catalyst prior to and/or during contact of the catalyst with an oxidative atmosphere, either in the initial preparation of the catalyst or in the regeneration of a used catalyst. Moreover, the electric current may also be applied to the catalyst continuously or periodically prior to and/or during use of the catalyst.

EXAMPLES

The following examples demonstrate the benefits of electrical activation of the catalyst prior to contacting the catalyst with a hydrocarbon (EA).

Example 1

Synthesis of $Mo_{1.0}V_{0.3}Te_{0.23}Nb_{0.17}Pd_{0.01}O_x$ 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotary evaporator flask. Then 200 mL of an aqueous solution of ammonium niobium oxalate (0.17M Nb), oxalic acid (0.155M), palladium nitrate hydrate (0.01M Pd), and nitric acid (0.24M $HNO_3$) was added thereto. After removing the water via a rotary evaporator with a warm water bath at 50° C. and 28 mm Hg (3700 Pa), the solid materials were further dried in a vacuum oven at 25° C. overnight and then calcined. Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. The final catalyst had a nominal composition of $Mo_{1.0}V_{0.3}Te_{0.23}Nb_{0.17}Pd_{0.01}O_x$. 30g of the catalyst were ground and added to 100 mL solution of 30% oxalic acid in water. The resulting suspension was stirred at 125° C. for 5 hrs in a Parr™ pressure reactor, then the solids were collected by gravity filtration and dried in a vacuum oven overnight at 25° C.

Example 2

The dried material from Example 1, sized to ≦75 microns, was sprayed through a Nordson Versa-Spray™ II gun, which is a standard model commonly used to apply organic powder coatings to metal and other substrates. The charge level was negative sixty (−60) kilovolts. The air pressure was approximately 10 psi (ca. 69 kPa).

In this electrostatic spray process the particles are electrostatically charged by the spray gun. Charging of the particles in the spray gun is effected by means of an applied voltage. In the corona charging system which was used, high voltage is applied to the gun's charging electrode and a strong electric field is created between the gun and ground. Corona discharge is a type of cold plasma that results in billions of electrons produced in the corona area and injected in the space between the gun and ground. (See *Powder Coating: The Complete Finisher's Handbook*, $2^{nd}$ ed., The Powder Coating Institute (1999)) It is believed that these electrons attach themselves to air molecules thereby creating negatively charged ions, and that, if the electric field outside corona discharge is sufficiently strong, the ions, in turn, attach themselves to solid particles.

Comparative Example A

The catalyst from example 1 (5 cc of 14–30 mesh (595–1400 μm) particles) was charged to a 0.5 inch (1.27 cm) ID stainless steel, tubular reactor and evaluated with a feed of 7% propane, 23% steam and balance air at 1 atm ($1.01×10^5$ Pa), 370° C. and 2400 GHSV (gas hourly space velocity, $hr^{-1}$). Steady state results were 74.5% propane conversion, 68.7% acrylic acid selectivity and 51.2% acrylic acid yield.

Comparative Example A1

The catalyst from example 1 (5 cc of 14–30 mesh (595–1400 μm) particles) was charged to a 0.5 inch (1.27 cm) ID stainless steel, tubular reactor and evaluated with a feed of 7% propane, 23% steam and balance air at 1 atm ($1.01×10^5$ Pa), 325° C. and 2400 GHSV. Steady state results were 62.8% propane conversion, 73.9% acrylic acid selectivity and 46.4% acrylic acid yield.

Example 3

The catalyst from example 2 (5 cc of 14–30 mesh (595–1400 μm) particles) was charged to a 0.5 inch (1.27 cm) ID stainless steel, tubular reactor and evaluated with a feed of 7% propane, 23% steam and balance air at 1 atm ($1.01 \times 10^5$ Pa), 348° C. and 2400 GHSV. Steady state results were 62.8% propane conversion, 79.0% acrylic acid selectivity and 49.6% acrylic acid yield.

Comparing example A1 with example 3, at comparable propane conversions of 63%, shows that the catalyst that was electrically activated prior to the oxidation is more selective and therefore provides a higher AA yield.

The following examples demonstrate the benefits of electrical activation during catalysis, i.e., during the oxidation reaction (EAC).

Example 4

To a 125 mL Parr™ Acid Digestion Bomb with an inner tube made of PTFE, 3.15 g of tellurium dioxide and 60 mL of 0.143M ammonium heptamolybdate tetrahydrate in water were added. The mixture was first hydrothermally treated at 100° C. for 1.5 hrs, and then 6 mL of 0.1M palladium nitrate hydrate in water and 6.5 g of vanadyl sulfate hydrate were added to the bomb at 60° C. followed by 30 mL of aqueous solution (0.2M in Nb) of ammonium niobium oxalate with stirring. The bomb contents were hydrothermally treated at 175° C. for 4 days. Black solids formed in the bomb were collected by gravity filtration, washed with deionized water (50 mL), dried in a vacuum oven at 25° C. overnight, and then calcined in air from 25 to 275° C. at 10° C./min and held at 275° C. for 1 hour, then in argon from 275 to 600° C. at 2° C./min and held at 600° C. for 2 hours. The final catalyst had a nominal composition of $Pd_{0.01}Mo_{1.0}V_{0.43}Te_{0.33}Nb_{0.1}O_x$.

Example 5

To a 20 ppi alpha alumina foam provided by Vesuvius™ Hi-Tech with the dimensions of 0.5 inch (1.27 cm) diameter and a length of 2.5 inches (6.35 cm) were attached electrodes. The silver electrodes were attached to the supporting foam by using a conductive silver paste. The silver metal wire was wrapped several times around the two ends of the foam. Extra wire length was left to attach alligator clips. The silver paste was applied generously onto the wiring area. The binder was burnt off in the silver paste to form a good contact using a furnace and following an annealing procedure in a nitrogen environment by heating from ambient to 150° C., 10° C./min. ramp rate, holding for 15 minutes; 150° C. to 600° C., 10° C./min ramp rate, holding for 1 hr.; and cooling to ambient temperature before removing the foam from furnace. 10 g of the calcined catalyst powder from example 1 above was added to 50 cc of isopropanol, HPLC grade. The mixture was placed in an ultrasonic bath at ambient temperature for at least 30 minutes. Continuous stirring (using a magnetic stir bar and stirring plate) at moderate rate was used to prevent powder from settling. Prior to wash coating, the weight of the foam with the electrode attachments was recorded. The supporting foam was warmed using a small oven set to about 70° C. Using a small pipette to draw the stirring catalyst mixture, droplets were applied on the foam starting from one end in the vertical position until the liquid exited on the other end. The process was repeated starting with the other end. The foam was then positioned horizontally and the catalyst mixture was applied along the outer edge. The foam was rotated frequently to ensure even application. The wetted foam was placed in a beaker in a small oven (heated to 70° C.) for 20–30 minutes. The wet-dry process cycles were repeated until no further weight change was observed.

Example 6

The wash coated ceramic piece made in Example 5 was inserted into a 0.5 inch (1.27 cm) diameter quartz tube reactor and evaluated in a fixed bed reactor with a feed composition of 7 mole % propane, 23 mole % water and balance air with a contact time of 3 seconds at a catalyst foam temperature of 300° C. The reactor effluent was analyzed by an on-line gc method to determine the conversion of feed components, product selectivity and yield. Initial base case equilibration studies were conducted without applying an electrical current. The steady state data over four hours indicated the following results: 23% propane conversion, 60% AA selectivity, and 14% AA yield. All mass balances fell between 99 and 101%.

Example 7

The same wash coated ceramic piece of example 6 was evaluated at the same reaction conditions as described in example 6 with the added electrical current of 0.03 amps, 242 volts, and 6 Watts. The resistance measured on the catalyst was 7.17 kilo Ohms. The steady state data over four hours with the electrical current applied was 61% propane conversion, 64% AA selectivity and 39% AA yield. Again all mass balances fell between 99 and 101%. Thus the EAC resulted in a higher conversion of propane, AA selectivity and yield over the base case (example 6). Electrical activation during catalysis (EAC) favors lower reactor bed temperatures (e.g. 300° C.) due to the highly effective electrical activation of the catalytic sites during the reaction process. At higher run temperatures the exothermicity of the reaction with EAC is difficult to control and non-selective, with over-oxidation occurring. This undesirable chemistry at the higher run temperatures leads to lower AA yield and $CO_x$ formation.

Comparative Example B

The catalyst from Example 4 (5 cc) was charged to a 0.5 inch (1.27 cm) ID stainless steel, tubular reactor and evaluated with a feed of 7% propane, 23% steam and balance air at 1 atm ($1.01 \times 10^5$ Pa), 370° C. and 2400 GHSV. Steady state results were 74.1% propane conversion, 67.2% acrylic acid selectivity and 49.8% acrylic acid yield.

Comparing the results of examples 6, 7 and example B shows that the propane conversion, AA selectivity and AA yield are lower for examples 6 and 7 as compared to example B. This can be partially explained by the higher operating temperature of example B which would lead to higher propane conversion. In addition, the wash coat catalysts of example 6 and 7 consist of one-third the amount of powder catalyst used in the pelletized fixed bed of example B. The greater amount of catalyst charge in example B would also lead to greater propane conversion. The slightly lower AA selectivity for examples 6 and 7 as compared to example B may be explained by a slightly unfavorable support effect of the alpha alumina foam with the catalyst powder in examples 6 and 7. Moreover, at lower operating temperatures (300° C. vs. 370° C.) the byproduct selectivities of acetic and propionic acid are slightly higher and therefore AA selectivities are lower.

The results of examples A and B are comparable at the same catalyst evaluation conditions. This is expected since the catalyst compositions are nearly identical. There are very slight variations in the stoichiometries of V, Te and Nb. Their catalyst characterization properties are very similar (XRD, XPS, EXAFS, SA, porosity). The catalyst of example A was prepared on a rotary evaporator while the catalyst of example B was prepared hydrothermally. The fact that the catalysts of examples A and B perform comparably allows us to make comparisons between electrical activation prior to oxidation (EA) and electrical activation during oxidation (EAC).

Comparing examples 3 and 7 shows that electrical activation prior to oxidation (EA) and electrical activation during catalysis (EAC) result in very similar propane conversion levels (63 vs. 61%). However, the AA selectivity and yield are notably greater for EA than for EAC.

The results from the above examples are summarized in Table 1 below. A 0.5 inch (1.27 cm), tubular reactor was used for evaluation with a feed of 7% propane, 23% steam and balance air at 1 atm (1.01×10$^5$ Pa) and 2400 GHSV.

TABLE 1

| Example | Bed type[1] | Activation?[2] | Bed temp, ° C. | % C3 conversion | % AA selectivity | % AA yield |
|---|---|---|---|---|---|---|
| Comp. A | packed | no | 370 | 74.5 | 68.7 | 51.2 |
| Comp. A1 | packed | no | 325 | 62.8 | 73.9 | 46.4 |
| Comp. B | packed | no | 370 | 74.1 | 67.2 | 49.8 |
| 3 | packed | EA | 348 | 62.8 | 79.0 | 49.6 |
| 6 | foam, | no | 300 | 23 | 60 | 14 |
| 7 | foam | EAC | 300 | 61 | 64 | 39 |

Footnotes:
[1]Bed type: packed refers to 5 cc of 14–30 mesh particles; foam refers to the calcined catalyst wash coated onto the foam.
[2]EA refers to electrical activation prior to oxidation by employing an electrostatic spray process with negative sixty kilovolts to the calcined catalyst. EAC refers to applying an electric current during catalysis.

Example 8

The supported catalyst prepared in accordance with Example 5 was used in the reactor apparatus and at the reaction conditions of Example 7, with electric current applied in accordance with the present invention, at 0.02 amps, 174 volts and 4 Watts. The resistance measured on the supported catalyst was 8.65 kilo Ohms. The results were analyzed using on-line GC analysis. Steady-state data over a four hour period resulted in 39% propane conversion, 70% AA selectivity and 27% AA yield.

Example 9

The supported catalyst prepared in accordance with Example 5 was used in the reactor apparatus and at the reaction conditions of Example 7, with electric current applied in accordance with the present invention, at 0.02 amps, 156 volts and 3 Watts. The resistance measured on the supported catalyst was 8.65 kilo Ohms. The results were analyzed using on-line GC analysis. Steady-state data over a four hour period resulted in 35% propane conversion, 70% AA selectivity and 24% AA yield.

Example 10

The supported catalyst prepared in accordance with Example 5 was used in the reactor apparatus and at the reaction conditions of Example 7, with electric current applied in accordance with the present invention, at 0.01 amps, 19 volts and 1 Watts. The resistance measured on the supported catalyst was 1.9 kilo Ohms. The results were analyzed using on-line GC analysis. Steady-state data over a four hour period resulted in 23% propane conversion, 67% AA selectivity and 15% AA yield.

The results of Examples 6–10 are summarized in Table 2 below, which shows that application of electrical current to the catalyst during catalytic oxidation (EAC), in accordance with the present invention, provides improved results (i.e., higher AA yield) compared to using the same catalyst, under the same reaction conditions, but without electrical current.

TABLE 2

| Example | Current (Amps) | % Propane Conversion | % AA Selectivity | % AA Yield |
|---|---|---|---|---|
| 6 | 0 | 23 | 60 | 14 |
| 7 | 6 | 61 | 64 | 39 |
| 8 | 4 | 39 | 70 | 27 |
| 9 | 3 | 35 | 70 | 24 |
| 10 | 1 | 23 | 67 | 15 |

The following examples demonstrate the oxidative dehydrogenation of propane to propene, using the catalyst of Example 5 and the reactor apparatus and the reaction conditions of Example 7.

Comparative Example C

Without application of electric current in accordance with the present invention, the given catalyst was used at the given run conditions (feed stream to the fixed bed reactor was 7 mole % propane, 23 mole % water and balance air; contact time was 3 seconds at a catalyst foam temperature (i.e., reaction temperature) of 300° C.). The results were analyzed using on-line GC analysis. Steady-state data over a four hour period resulted in 23% propane conversion, 6.5% propylene selectivity and 1.5% propylene yield.

Example 11

The supported catalyst was used in the above-described reactor apparatus at the above-identified reaction conditions, with electric current applied in accordance with the present invention, at 0.03 amps, 242 volts and 6 Watts. The resistance measured on the supported catalyst was 7.17 kilo Ohms. The results were analyzed using on-line GC analysis. Steady-state data over a four hour period resulted in 61% propane conversion, 7% propylene selectivity and 4% propylene yield.

The following hypothetical examples demonstrate the oxidative dehydrogenation of isobutane to isobutene, using the catalyst of Example 5 and the reactor apparatus and the reaction conditions of Example 7.

Comparative Example D

Without application of electric current in accordance with the present invention, the given catalyst is run at the revised run conditions (feed stream to the fixed bed reactor was 7 mole % isobutane, 23 mole % water and balance air; contact time was 3 seconds at a catalyst foam temperature (i.e., reaction temperature) of 300° C.). The results may be analyzed using on-line GC analysis. Steady-state data over a four hour period may result in 30–40% isobutane conversion, 10–30% isobutene selectivity and 3–12% isobutene yield.

Example 12

The supported catalyst prepared in accordance with the above-described procedures may be used in the above-described reactor apparatus at the above-proposed reaction conditions, with electric current applied in accordance with the present invention, at 0.03 amps, 242 volts and 6 Watts. The resistance measured on the supported catalyst may be 7.17 kilo Ohms. The results may be analyzed using on-line GC. Steady-state data over a four hour period may result in 60–80% isobutane conversion, 35–60% isobutene selectivity and 21–48% isobutene yield.

What is claimed is:

1. A method for enhancing the production of an oxidative reaction product of a hydrocarbon comprising:
  providing an electrically conductive catalyst composition comprising a vapor phase partial oxidation catalyst;
  subjecting said electrically conductive catalyst composition to an electric current passing through said electrically conductive catalyst composition;
  passing a hydrocarbon vapor over said electrically conductive catalyst composition;
  wherein said vapor phase partial oxidation catalyst comprises a mixed metal oxide having the following empirical formula $A_aM_mN_nX_xO_o$ wherein
  A is at least one element selected from the group consisting of Mo and W,
  M is at least one element selected from the group consisting of V and Ce,
  N is at least one element selected from the group consisting of Te, Se and Sb,
  X is at least one element selected from the group consisting of Nb, Ta, Ti, Al, Zr, Cr, Mn, Fe, Ru, Co, Rh, Ni, Pt, Bi, B, In, As, Ge, Sn, Li, Na, K, Rb, Cs, Fr, Be, Mg, Ca, Sr, Ba, Hf, Pb, P, Pm, Eu, Gd, Dy, Ho, Er, Th, Yb, Lu, Au, Ag, Pd, Ga, Pr, Re, Ir, Nd, Y, Sm and Tb,
  wherein
  when a=1, m=0.01 to 1.0, n=0.01 to 1.0, x=0.001 to 1.0 and o is dependent on the oxidation state of the other elements;
  and wherein said electrically conductive catalyst composition is subjected to said electric current prior to contacting the hydrocarbon vapor.

2. The method according to claim 1, wherein said electrically conductive catalyst composition comprises nanoparticles of said mixed metal oxide having the following empirical formula $A_aM_mN_nX_xO_o$ wherein
  A is at least one element selected from the group consisting of Mo and W,
  M is at least one element selected from the group consisting of V and Ce,
  N is at least one element selected from the group consisting of Te, Se and Sb,
  X is at least one element selected from the group consisting of Nb, Ta, Ti, Al, Zr, Cr, Mn, Fe, Ru, Co, Rh, Ni, Pt, Bi, B, In, As, Ge, Sn, Li, Na, K, Rb, Cs, Fr, Be, Mg, Ca, Sr, Ba, Hf, Pb, P, Pm, Eu, Gd, Dy, Ho, Er, Th, Yb, Lu, Au, Ag, Pd, Ga, Pr, Re, Ir, Nd, Y, Sm and Tb,
  wherein
  when a=1, m=0.01 to 1.0, n=0.01 to 1.0, x=0.001 to 1.0 and o is dependent on the oxidation state of the other elements.

3. The method according to claim 1, wherein said electrically conductive catalyst composition comprising a vapor phase partial oxidation catalyst is coated on a channel wall of a microchannel reactor.

4. A method for altering the oxidative reaction product of a vapor phase catalytic oxidation comprising:
  providing an electrically conductive catalyst composition comprising a vapor phase partial oxidation catalyst;
  subjecting said electrically conductive catalyst composition to a first electric current passing through said electrically conductive catalyst composition, said first electric current favoring the production of a partial oxidation reaction product of a first hydrocarbon;
  passing said first hydrocarbon over said electrically conductive catalyst composition;
  recovering said partial oxidation reaction product of said first hydrocarbon;
  ceasing passage of said first hydrocarbon over said electrically conductive catalyst composition; subjecting said electrically conducting catalyst composition to a second electric current passing through said electrically conductive catalyst composition, said second electric current favoring the production of a partial oxidation reaction product of a second hydrocarbon passing said second hydrocarbon over said electrically conductive catalyst composition;
  recovering said partial oxidation reaction product of said second hydrocarbon;
    wherein said electrically conductive catalyst composition is subjected to said first electric current prior to contacting the first hydrocarbon; and said electrically conductive catalyst composition is subjected to said second electric current prior to contacting the second hydrocarbon.

5. The method according to claim 4, wherein said electrically conductive catalyst composition comprises a mixed metal oxide of the following empirical formula $A_aM_mN_nX_xO_o$ wherein
  A is at least one element selected from the group consisting of Mo and W,
  M is at least one element selected from the group consisting of V and Ce,
  N is at least one element selected from the group consisting of Te, Se and Sb,
  X is at least one element selected from the group consisting of Nb, Ta, Ti, Al, Zr, Cr, Mn, Fe, Ru, Co, Rh, Ni, Pt, Bi, B, In, As, Ge, Sn, Li, Na, K, Rb, Cs, Fr, Be, Mg, Ca, Sr, Ba, Hf, Pb, P, Pm, Eu, Gd, Dy, Ho, Er, Th, Yb, Lu, Au, Ag, Pd, Ga, Pr, Re, Ir, Nd, Y, Sm and Tb,
  wherein
  when a=1, m=0.01 to 1.0, n=0.01 to 1.0, x=0.001 to 1.0 and o is dependent on the oxidation state of the other elements.

6. A method for enhancing the production of an oxidative reaction product of a hydrocarbon comprising:
  providing an electrically conductive catalyst composition comprising a vapor phase partial oxidation catalyst;

subjecting said electrically conductive catalyst composition to an electric current passing through said electrically conductive catalyst composition;
passing an oxidative gas over said electrically conductive catalyst;
then, passing a hydrocarbon vapor over said electrically conductive catalyst composition;
and wherein said electrically conductive catalyst composition is subjected to said electric current prior to contacting the hydrocarbon vapor.

7. The method according to claim 6, wherein the electrically conductive catalyst composition comprises a mixed metal oxide having the following empirical formula $$A_a M_m N_n X_x O_o$$

wherein

A is at least one element selected from the group consisting of Mo and W,

M is at least one element selected from the group consisting of V and Ce,

N is at least one element selected from the group consisting of Te, Se and Sb,

X is at least one element selected from the group consisting of Nb, Ta, Ti, Al, Zr, Cr, Mn, Fe, Ru, Co, Rh, Ni, Pt, Bi, B, In, As, Ge, Sn, Li, Na, K, Rb, Cs, Fr, Be, Mg, Ca, Sr, Ba, Hf, Pb, P, Pm, Eu, Gd, Dy, Ho, Er, Th, Yb, Lu, Au, Ag, Pd, Ga, Pr, Re, Ir, Nd, Y, Sm and Tb, wherein when a=1, m=0.01 to 1.0, n=0.01 to 1.0, x=0.001 to 1.0 and o is depenedent on the oxidation state of the other elements.

8. The method according to claim 6, wherein said electrically conductive catalyst composition comprises nanoparticles comprising a mixed metal oxide of the following empirical formula $$A_a M_m N_n X_x O_o$$

wherein

A is at least one element selected from the group consisting of Mo and W,

M is at least one element selected from the group consisting of V and Ce,

N is at least one element selected from the group consisting of Te, Se and Sb,

X is at least one element selected from the group consisting of Nb, Ta, Ti, Al, Zr, Cr, Mn, Fe, Ru, Co, Rh, Ni, Pt, Bi, B, In, As, Ge, Sn, Li, Na, K, Rb, Cs, Fr, Be, Mg, Ca, Sr, Ba, Hf, Pb, P, Pm, Eu, Gd, Dy, Ho, Er, Th, Yb, Lu, Au, Ag, Pd, Ga, Pr, Re, Ir, Nd, Y, Sm and Tb, wherein when a=1, m=0.01 to 1.0, n=0.01 to 1.0, x=0.001 to 1.0 and o is dependent on the oxidation state of the other elements.

9. The method according to claim 6, wherein said electrically conductive catalyst composition comprising a vapor phase partial oxidation catalyst is coated on a channel walls of a microchannel reactor.

* * * * *